US012661237B2

(12) United States Patent 
Siccardi et al.

(10) Patent No.: US 12,661,237 B2 
(45) Date of Patent: Jun. 23, 2026

(54) EXPANDABLE INTERVERTEBRAL CAGE

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Marco Riva, Castel San Pietro (CH); Samuele Meroni, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 216 days.

(21) Appl. No.: 18/576,047

(22) PCT Filed: Jul. 6, 2022

(86) PCT No.: PCT/IB2022/056235 
§ 371 (c)(1), 
(2) Date: Jan. 2, 2024

(87) PCT Pub. No.: WO2023/281409 
PCT Pub. Date: Jan. 12, 2023

(65) Prior Publication Data 
US 2024/0307191 A1 Sep. 19, 2024

(30) Foreign Application Priority Data 
Jul. 6, 2021 (IT) ........................ 102021000017747

(51) Int. Cl. 
A61F 2/44 (2006.01) 
A61F 2/30 (2006.01)

(52) U.S. Cl. 
CPC .... *A61F 2/447* (2013.01); *A61F 2002/30261* (2013.01); *A61F 2002/30433* (2013.01)

(58) Field of Classification Search 
CPC ...... A61F 2/44–447; A61F 2002/30261; A61F 2002/30433 
See application file for complete search history.

(56) References Cited

U.S. PATENT DOCUMENTS

| 6,176,882 B1 * | 1/2001 | Biedermann | ........... A61F 2/447 |
| | | | 623/17.11 |
| 10,022,239 B1 | 7/2018 | Lentner et al. | |

(Continued)

OTHER PUBLICATIONS

English translation of Notice of Reasons for Refusal for Japanese Application No. 2024-500426 dated Mar. 19, 2025, 5 pages.

(Continued)

*Primary Examiner* — Nicholas J Plionis 
(74) *Attorney, Agent, or Firm* — Meunier Carlin & Curfman LLC

(57) ABSTRACT

An expandable intervertebral cage includes a first plate and a second plate opposite to the first one. The cage further comprises a movement and adjustment mechanism of the two plates suitable to promote the relative mutual translation between the first and second plate parallel to each other. The movement and adjustment mechanism comprises a single central shaft, coaxial with a central longitudinal axis of the plates and having an external thread, a proximal wedge and a distal wedge placed between the first and second plate, aligned along the central longitudinal axis and coupled to the external thread of the central shaft which is centrally inserted in the distal wedge and the proximal wedge. The movement and adjustment mechanism also comprises a first actuator and a second actuator, both provided on the central shaft and placed at the same proximal end of the cage.

16 Claims, 7 Drawing Sheets

(56) References Cited

U.S. PATENT DOCUMENTS

| 10,285,824 | B2 | 5/2019 | Robinson |
| 10,441,430 | B2 | 10/2019 | Ludwig et al. |
| 2010/0305704 | A1* | 12/2010 | Messerli ................. A61F 2/442 |
| | | | 623/17.16 |
| 2019/0021873 | A1 | 1/2019 | Dmuschewsky |
| 2019/0133779 | A1* | 5/2019 | McLaughlin ....... A61F 2/30749 |
| 2020/0281741 | A1* | 9/2020 | Grotz ..................... A61F 2/447 |

OTHER PUBLICATIONS

International Search Report and Written Opinion issued in PCT/IB2022/056235, mailed Oct. 25, 2022.

* cited by examiner

EXPANDABLE INTERVERTEBRAL CAGE

FIELD OF APPLICATION

The present invention relates to an expandable intervertebral cage.

In particular, the implant object of the present invention is used in the treatment of spinal diseases in which the spacing out of two adjacent vertebral bodies is necessary, for example in the case of disc crushing, or in the presence of deformities of the vertebral column that can cause unnatural curvatures of the same, such as in the case of kyphosis or lordosis, to restore the correct curvature thereof.

PRIOR ART

In the prior art there are intravertebral surgical implants having a central body, called intervertebral cage, suitable to be inserted into the intervertebral space, by means of a special insertion tool.

These cages have an elongated shape and have two resting surfaces suitable to receive the vertebral bodies. Cages are used that have contact surfaces that can keep the surfaces parallel, while being able to translate with respect to each other to allow interdiscal and intervertebral spacing out, or that can vary their mutual inclination, in the event that the patient needs correction of the spinal curvature.

The known and currently used expandable intervertebral cages allow the surgeon to be able to space out the resting surfaces from each other in parallel or even to vary their mutual inclination, in kyphosis or in lordosis, by acting on appropriate adjustment mechanisms.

The surgeon can thus adjust the inclination of the resting surfaces to come as close as possible to the correction angle required to restore the correct curvature of the patient's spine.

However, the known expandable intervertebral cages have drawbacks due to the difficulty of actuating the adjustment mechanism of the surfaces themselves. The expandable intervertebral cages of known type have the possibility of varying the inclination of the surfaces by increasing the distance between them only in proximal position or only in distal position. This requires a duplication of the actuation mechanism, one in the proximal position and one in the distal position, with consequent difficulties in reaching the proximal mechanism because it is more internal. This implies the need to have a passage inside the cage with consequent increase in the dimension of the implant, which however is not compatible with the anatomical dimensions of the intervertebral space, or thinning of the thicknesses of the implant, in order to be able to contain the global dimensions of the same, which can cause fragility or instability of the device or tool used for the adjustment. This is for example the case of the intervertebral cage described in document U.S. Pat. No. 10,285,824, in which the adjustment mechanisms are placed in a distal and proximal position with a central hollow shaft, inside which the adjustment tool is inserted. The hole inside the central shaft has a reduced diameter, also considering the global dimensions of the cage, so the tool to be inserted will have an even smaller diameter: this makes it difficult to be able to apply the torque necessary to overcome the resistance opposed by the vertebrae that weigh down on the cage plates to avoid the risk of breaking the tool itself, which must be long and thin.

Other expandable intervertebral cages have movement mechanisms that are structurally complex to be actuated, like for example described in document U.S. Pat. No.

6,176,882, others still do not guarantee optimal stability of the final position of the resting surfaces and are designed to open by thrust, entailing stresses that can cause the breakage or the collapse of the cage, like for example the device described in U.S. Pat. No. 10,441,430.

The technical problem underlying the present invention is, therefore, to propose an expandable intervertebral cage that is capable of overcoming the drawbacks encountered in the prior art.

In particular, aim of the present invention is to propose an expandable intervertebral cage that allows a correction of the intervertebral distance and/or the curvature of the spine, to restore the correct anatomy of the patient, in an easy, simple and quick way for the surgeon.

A further aim of the present invention is to propose an expandable intervertebral cage that is compact, solid and allows the use of a special adjustment tool capable of overcoming the resistance offered by the vertebrae that weigh on the plates of the cage, without the surgeon having to apply excessive force and without the risk of breakage of the cage and of the adjustment tool.

Finally, aim of the present invention is to provide an expandable intervertebral cage that is structurally simple and allows for punctual adjustment of the plates in contact with the vertebrae.

These and other aims are achieved by an expandable intervertebral cage for spacing out two vertebral bodies of a vertebral column as described in the appended Claims.

SUMMARY OF THE INVENTION

In particular, the present invention relates to an expandable intervertebral cage for spacing out two vertebral bodies of a vertebral column comprising a first plate and a second plate opposite and facing each other, both having a planar conformation axially elongated along a central longitudinal axis that extends from a proximal end to a distal end of the cage itself.

The first and second plate comprising respective internal surfaces facing each other and respective external contact surfaces, the latter suitable to receive a respective vertebral body for resting. The cage further comprises a movement and adjustment mechanism of the first plate and the second plate suitable to promote the mutual translation of the first plate and the second plate parallel to each other, so as to vary the height of the cage to space out two adjacent vertebral bodies, and the rotation of the one with respect to the other around a respective hinge axis, arranged transversely to the central longitudinal axis of the cage and contained between the two plates, so as to vary the mutual inclination of the first and second plate to correct the deformation of the vertebral column. The movement and adjustment mechanism comprises a single central shaft, coaxial with the central longitudinal axis and having an external thread, a proximal wedge and a distal wedge placed between the first and second plate, aligned along the central longitudinal axis and coupled to the external thread of the central shaft which is centrally inserted in and passing through the distal wedge and the proximal wedge. The movement and adjustment mechanism also comprises a first actuator and a second actuator, both provided on the central shaft and placed at the same proximal end of the cage.

The term proximal refers to the portion of the cage closest to the surgeon and facing the surgeon's body when the surgeon holds the cage before placing it in the patient, while the term distal refers to the portion of the cage furthest from the surgeon and facing the patient's body.

The central shaft, suitable to rotate around the central longitudinal axis, has a single external thread having a single mono-directional winding direction extending throughout the external surface of the central shaft.

The distal wedge comprises a threaded portion suitable to be screwed onto the external thread of the central shaft.

The proximal wedge has therein an annular disc having a threaded portion which couples with the external thread of the central shaft.

The annular disc is contained inside the proximal wedge and rotates about the central shaft to promote the translation of the proximal wedge along the central longitudinal axis.

The first actuator and the second actuator can be actuated in a counter-rotating manner with respect to each other about the central longitudinal axis.

The proximal wedge and the distal wedge are movable both independently of each other and simultaneously, depending on the desired opening and relative position between the first plate and the second plate.

The first plate and the second plate each have two projecting portions, protruding from the respective internal surfaces which face each other and are turned internally the cage, having inclined planes along which the proximal wedge and the distal wedge slide to promote the movement of the first and the second plate in mutual translation and/or rotation.

The inclined planes of the projecting portions are converging towards a same middle portion of the cage, to define, with the inclined planes of the opposite plate, respective V-shaped housings, having a vertex oriented towards said middle portion of the cage and within which the proximal wedge and the distal wedge slide.

The inclined surfaces of the distal wedge and the proximal wedge abut and slide against the inclined planes of the projecting portions of the two plates, so that, following the translation of the two wedges along the central longitudinal axis, the relative coupling position between inclined surfaces and inclined planes varies, thus changing the relative position of the plates.

The first actuator is suitable to rotate the central shaft and move the distal wedge and the proximal wedge.

The second actuator is suitable to move only the proximal wedge.

The first actuator is placed at a proximal end of the central shaft.

The first actuator is defined by a polygonal housing axially made in the central shaft, for inserting a gripping and actuating tool.

The second actuator is placed inside the proximal wedge.

The second actuator is the annular disc fitted into the central shaft. Said annular disc has an internal thread which couples with the external thread of said central shaft. The annular disc is contained inside the proximal wedge and is free to rotate, by meshing the external thread of the central shaft, thereby dragging the proximal wedge in translation towards the proximal end or towards the middle portion of the cage.

The annular disc has gripping portions for engaging with a gripping and actuating tool.

The cage also has a containment and connection structure suitable to contain the movement and adjustment mechanism, the central shaft, the distal wedge and the proximal wedge and to connect the first and second plate with each other. This containment structure is interposed between the first and second plate in a perimeter position.

Two pins are also present, each one arranged transversely to the central longitudinal axis and contained between the two plates.

Each pin connects the respective plate to the containment and connection structure.

The two projecting portions of each between the first and second plate have, in a central position, a respective eylet extending orthogonally to the central longitudinal axis and elongated towards the opposite plate.

The two pins are inserted into the slots to allow moving the first and the second plate: the two plates translate parallel to each other moving mutually away from, and closer to each other, and rotate with respect to each other about the respective pin, to incline so as to diverge or converge towards the distal end. The pins remain in a fixed position while the plates translate thanks to the play offered by the elongated oval slots.

BRIEF DESCRIPTION OF THE DRAWINGS

The present invention will be made clearer by the following detailed description, with reference to the accompanying drawings provided by way of example only, wherein.

DETAILED DESCRIPTION

In the accompanying figures, 1 denotes as a whole an expandable intervertebral cage for spacing out two vertebral bodies in accordance with the present invention.

This cage is interposed between two adjacent vertebral bodies, in case of diseases of the vertebral column, to space them out in case of collapse or to correct their mutual angular position and restore the correct curvature of the vertebral column.

Figures 1, 2:
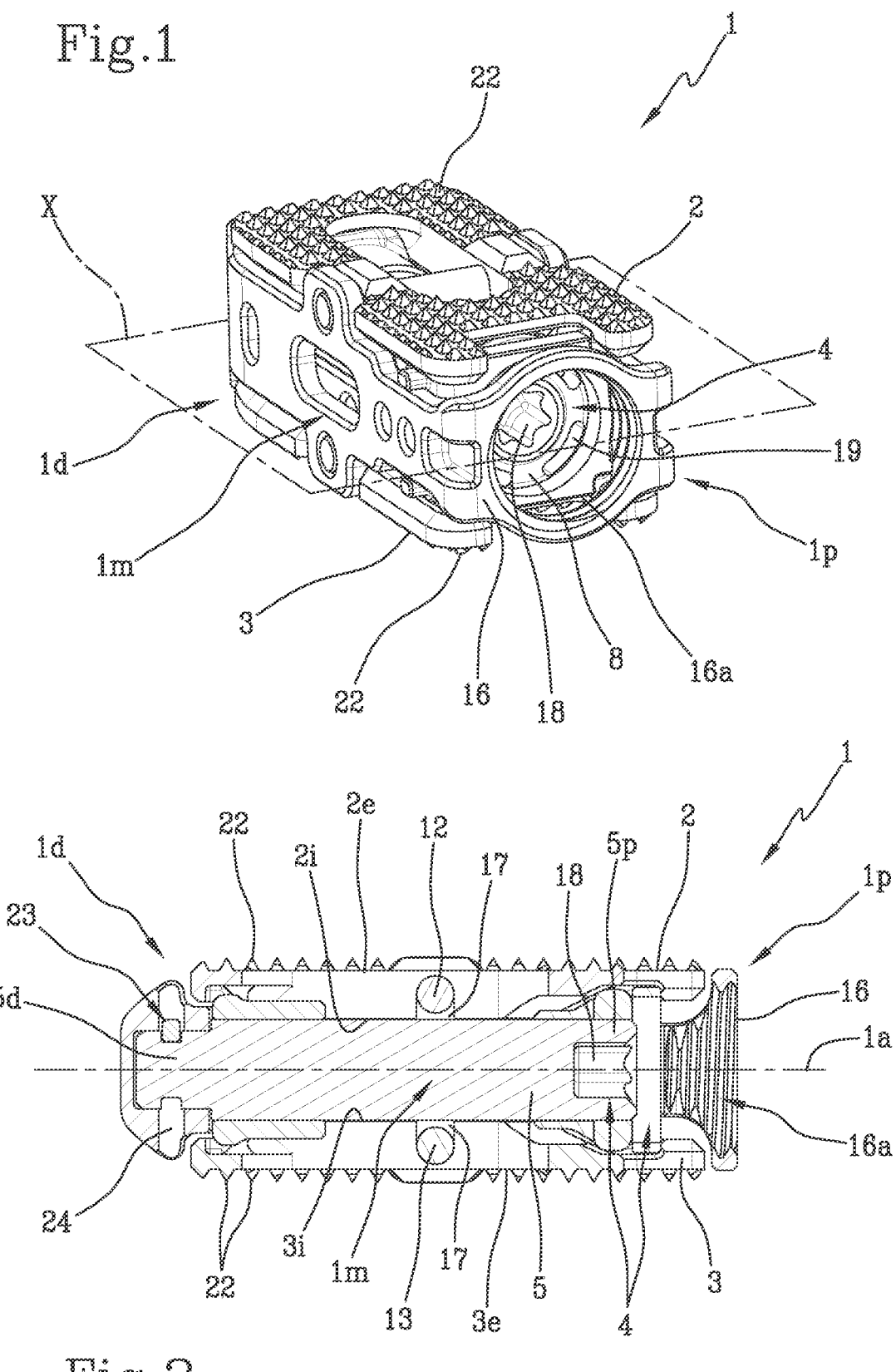
FIG. 1 shows a perspective view of an expandable intervertebral cage for spacing out two vertebral bodies in accordance with the present invention, in a non-operating position of total closure of the cage and with parallel plates.
FIG. 2 shows a side section view of the cage shown in FIG. 1.

As shown in FIG. 1, the expandable intervertebral cage in accordance with the present invention comprises a first plate 2 and a second plate 3, opposite to the first plate 2, both having planar conformation and facing each other. The first 2 and the second 3 plate have a planar conformation having elongated development mainly along a central longitudinal axis 1*a* of the cage 1, extending from a proximal end 1*p* to a distal end 1*d* of the cage 1.

The two plates each comprise respective internal surfaces 2*i* and 3*i*, facing each other, and respective external contact surfaces 2*e*, 3*e* suitable to receive a respective vertebral body for resting.

On these external surfaces 2*e* and 3*e*, pointed structures 22 are made, having for example a pyramidal conformation, protruding towards the outside of the cage to improve the grip on the respective vertebral bodies being coupled.

The cage 1 also comprises a movement and adjustment mechanism 4 of the first plate 2 and of the second plate 3, to allow mutual spacing out and/or variation of the relative inclination. In particular, the movement and adjustment mechanism 4 is suitable to space out the two plates 2 and 3 and to make them translate parallel to each other, so as to vary the height of the cage 1, and to rotate the first 2 and the second 3 plate around a respective hinge axis 1*b*, interposed between the two plates and transverse to the central longitudinal axis of the cage 1*a*, to vary the inclination of the two plates, and thus of the two external contact surfaces 2*e*, 3*e*, so as to correct the deformation of the vertebral column. The adjustment of the inclination of the two plates 2 and 3 can lead them to diverge, either towards the distal end 1*d* or towards the proximal end 1*p* of the cage 1, by a variable angle that can be determined at will, depending on the degree of correction to be given to the curvature of the vertebral column.

Figures 3, 4:
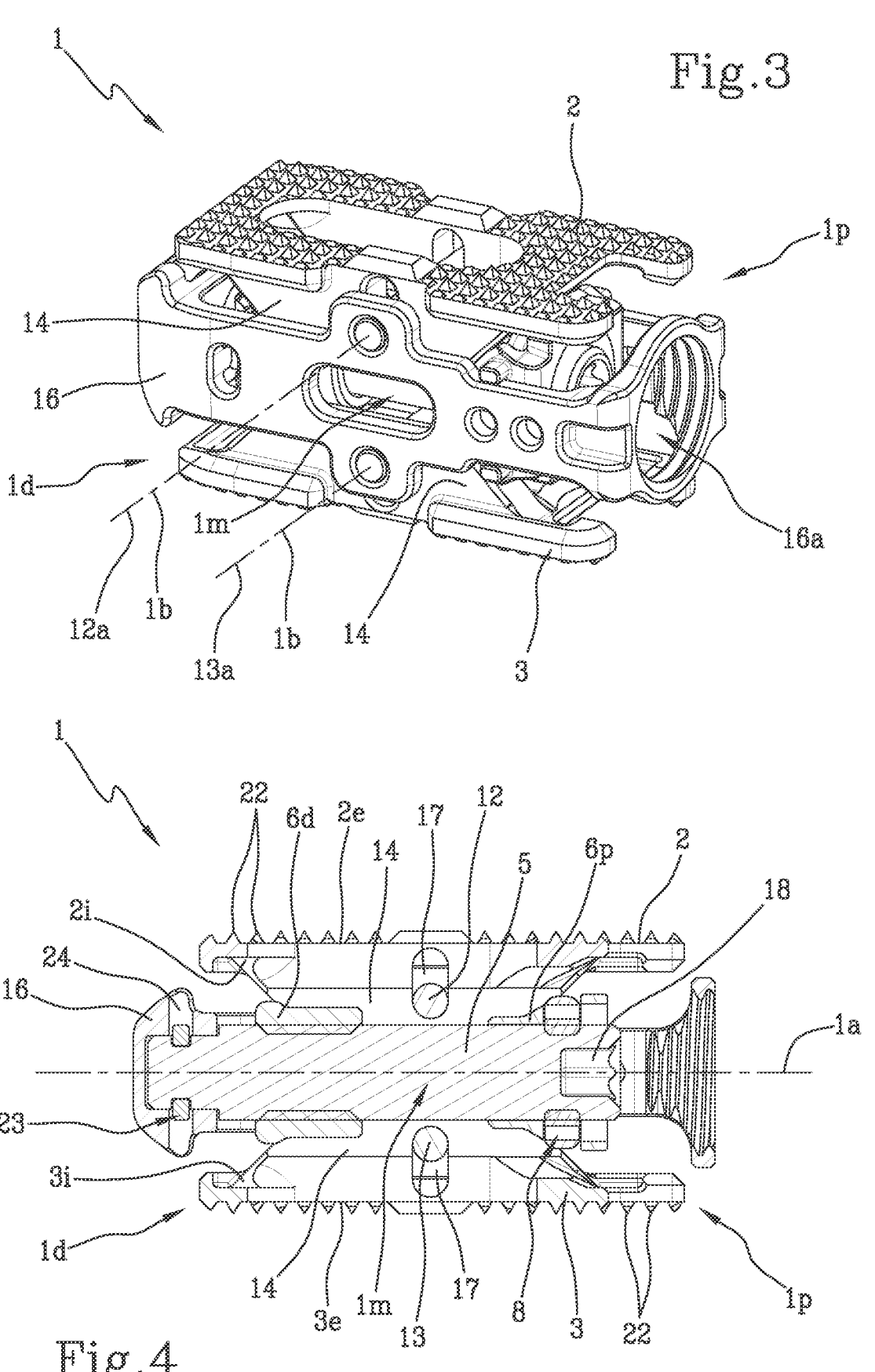
FIG. 3 shows a perspective view of the intervertebral cage in accordance with the present invention, in a first operating position having parallel spaced out plates.
FIG. 4 shows a side section view of the cage shown in FIG. 3.
Figure 5:
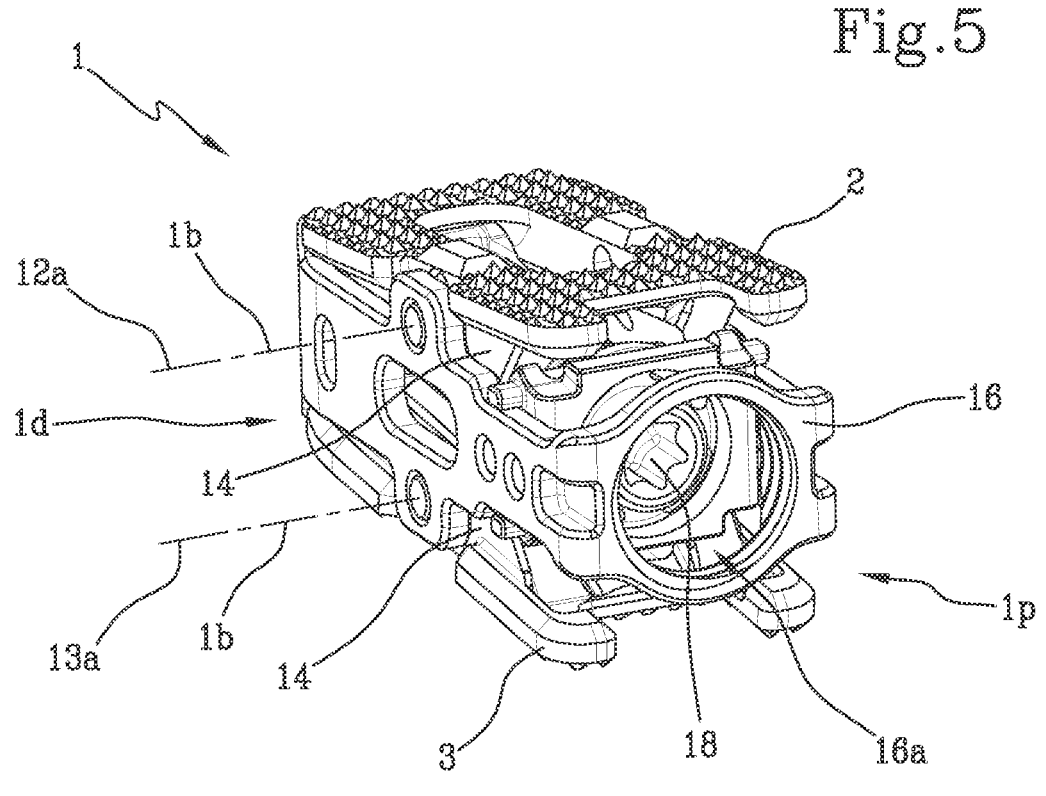
FIG. 5 shows a perspective view of the intervertebral cage in accordance with the present invention, in a second operating position having diverging plates in the distal direction.
Figure 6:
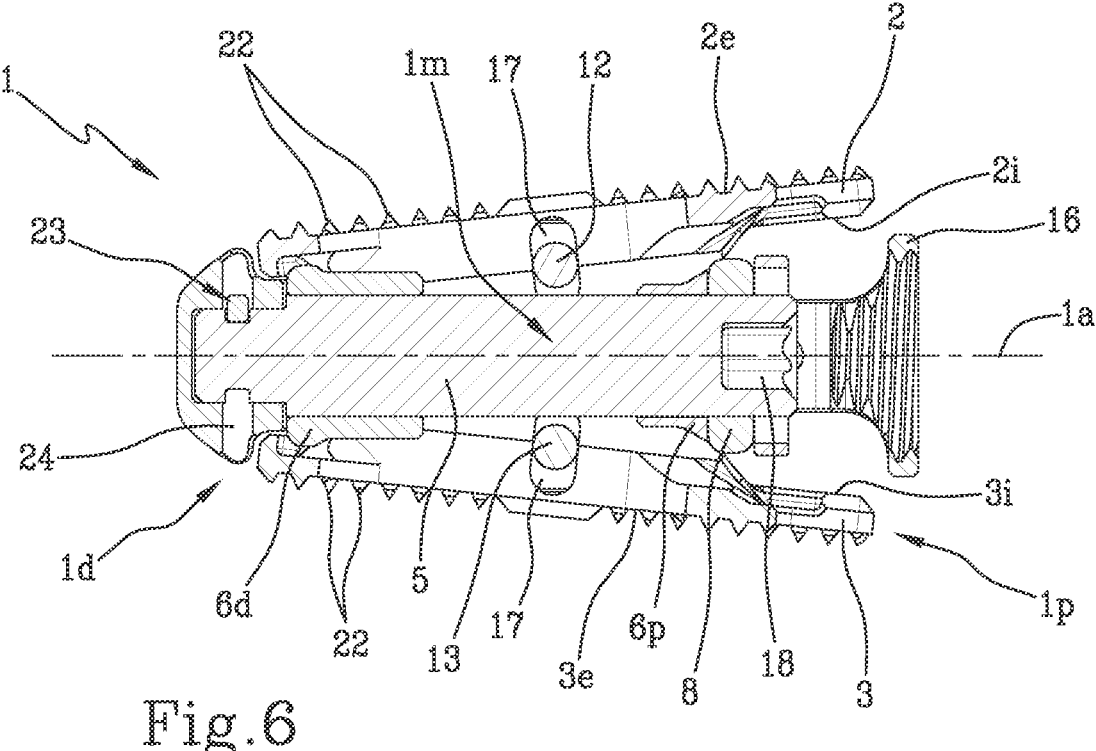
FIG. 6 shows a side section view of the cage shown in FIG. 5.
Figure 7:
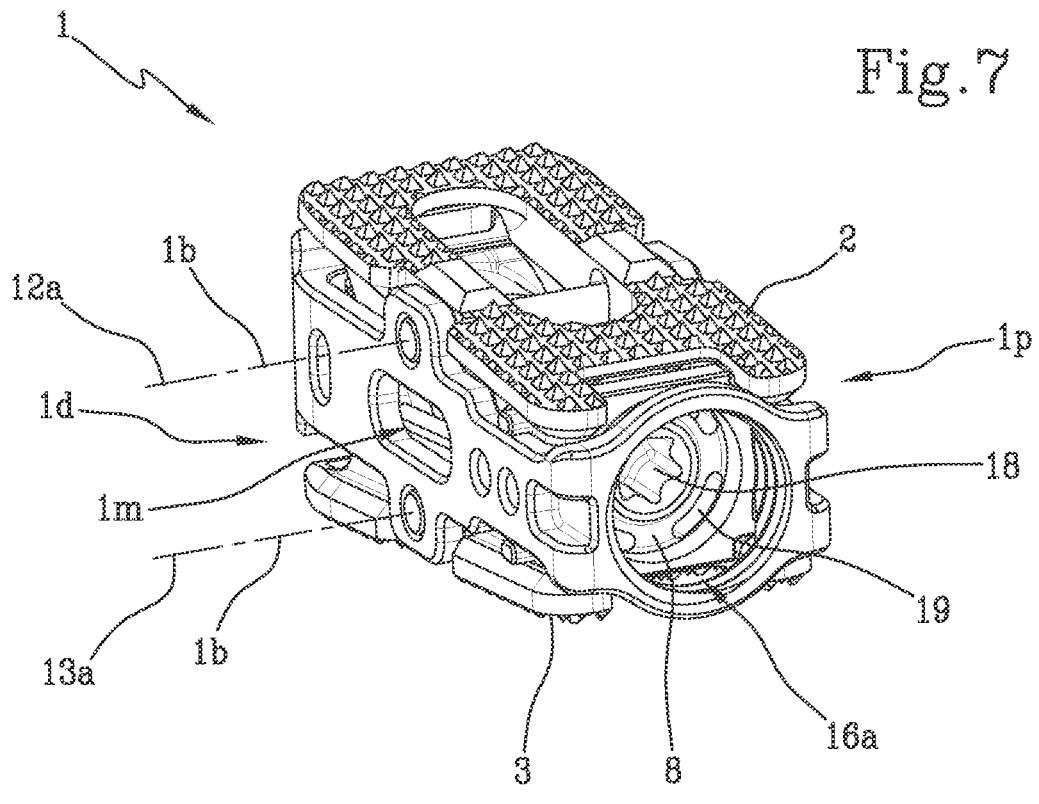
FIG. 7 shows a perspective view of the intervertebral cage in accordance with the present invention, in a third operating position having diverging plates in the proximal direction.
Figure 8:
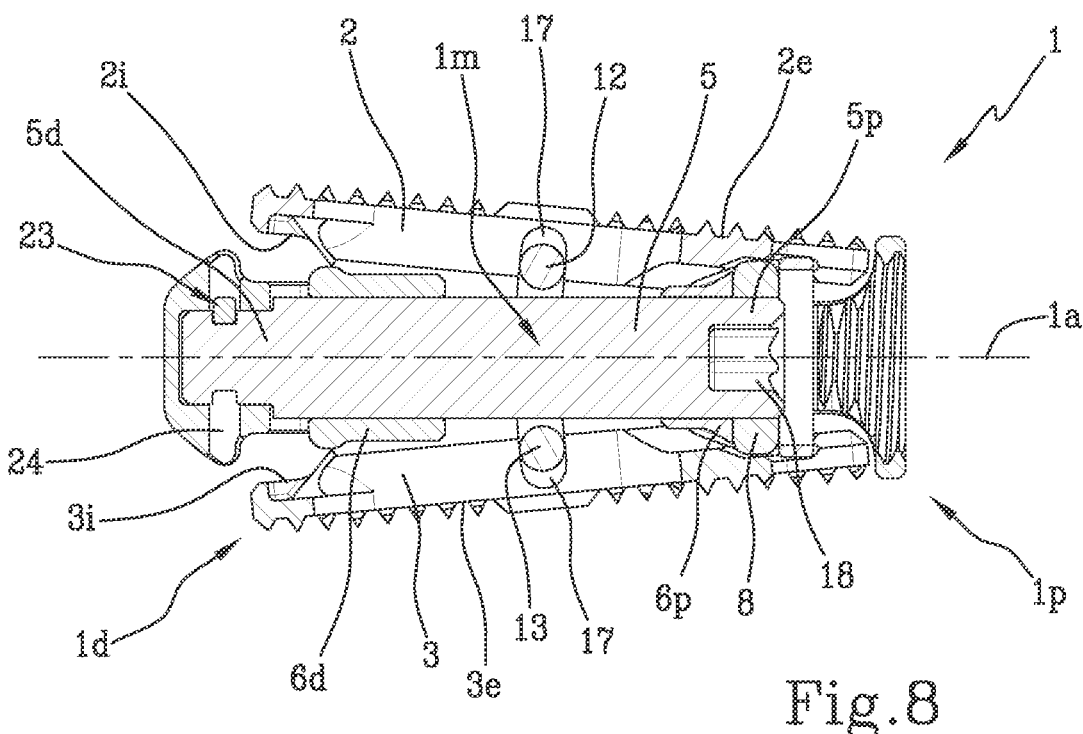
FIG. 8 shows a side section view of the cage shown in FIG. 7.
Figure 9:
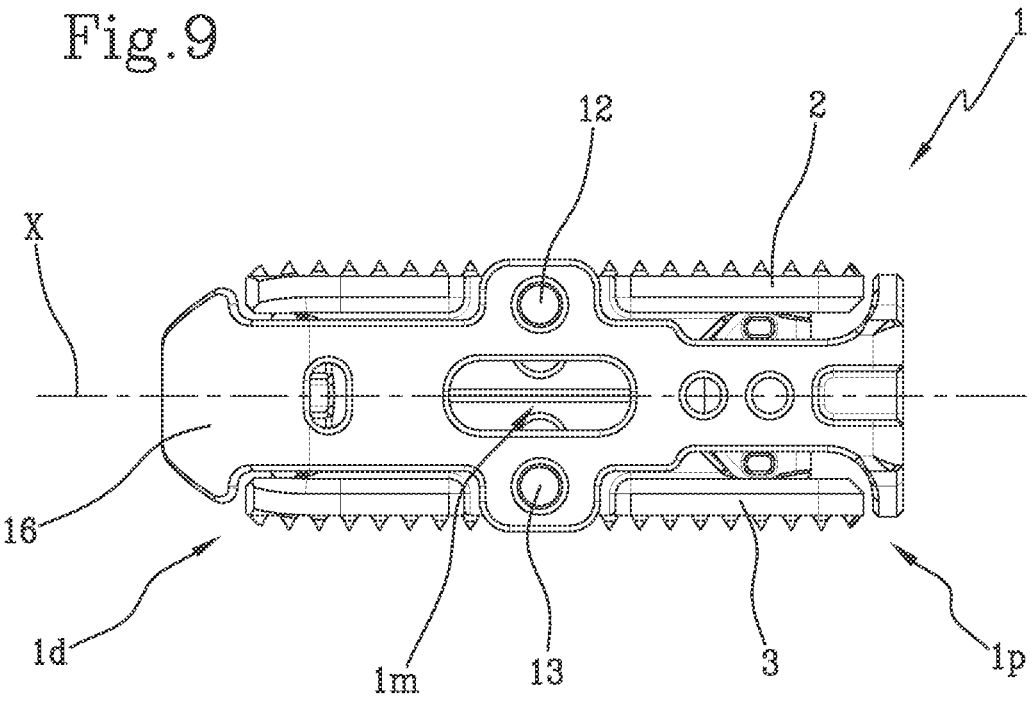
FIG. 9 shows a side view of the cage shown in FIG. 1.
Figure 10:
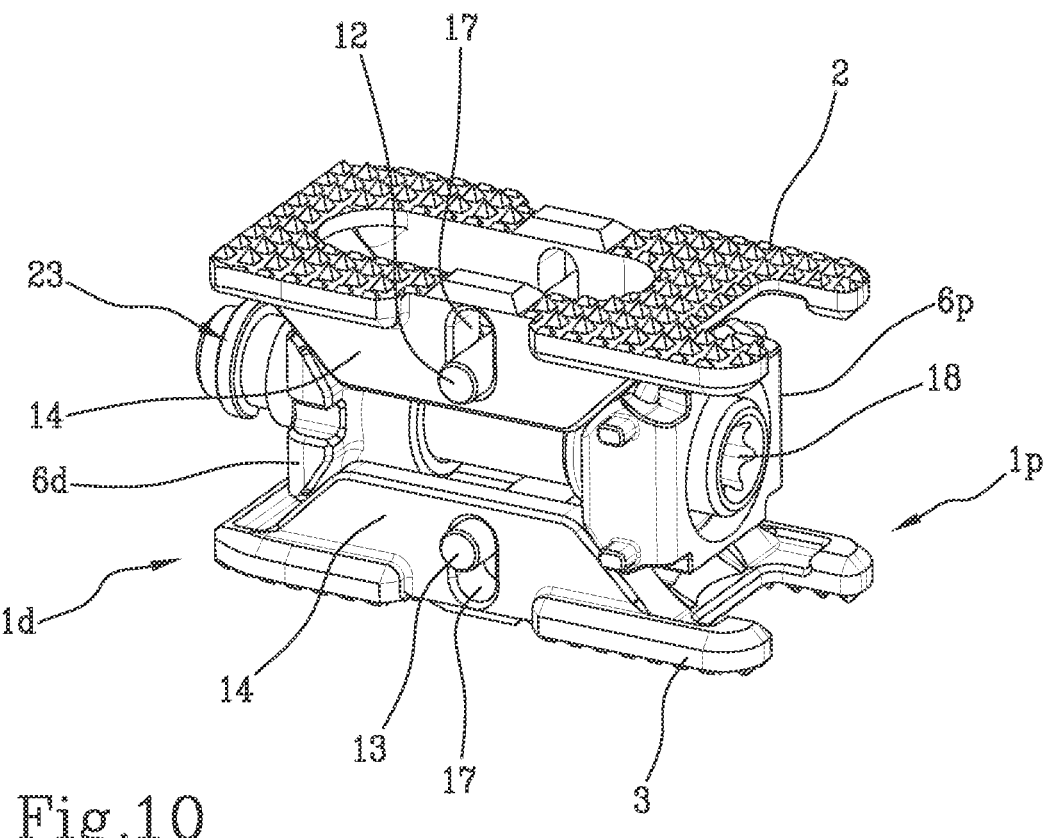
FIG. 10 shows a perspective view of the cage in FIG. 3 with some parts removed to make the internal structure visible.

The cage 1 may assume different configurations depending on the relative position between the two plates 2 and 3: a rest configuration, shown in FIGS. 1 and 2, in which the cage is completely closed and compact and the plates are in mutual approach and parallel to each other; a first operating configuration, shown in FIGS. 3 and 4, in which the cage is expanded and the plates are spaced out and parallel to each other; a second operating configuration, shown in FIGS. 5 and 6, in which the cage 1 is at least partially expanded and the plates are inclined at the same angle with respect to the central longitudinal axis 1*a*, so as to diverge towards the proximal end 1*p* of the cage; a third operating configuration, shown in FIGS. 7 and 8, in which the cage 1 is at least partially expanded and the plates are inclined at the same angle with respect to the central longitudinal axis 1*a*, so as to diverge towards the distal end 1*d* of the cage. As mentioned above, the amplitude of the angle defined between each plate 2 and 3 and the central longitudinal axis 1*a* may be varied as desired by the surgeon according to the surgical needs.

The movement and adjustment mechanism 4 comprises a single central shaft 5, coaxial with the central longitudinal axis 1*a*, having an external thread 5*f*, made on the external surface 5*s* of the shaft 5. This external thread 5*f* is continuous and has a single mono-directional winding direction and extends throughout the external surface 5*s* of the central shaft 5. The central shaft 5 is suitable to rotate, clockwise and counterclockwise, about the central longitudinal axis 1*a*.

The movement and adjustment mechanism 4 further comprises a proximal wedge 6*p* and a distal wedge 6*d* that are placed between the first 2 and the second 3 plate. The proximal wedge 6*p* and the distal wedge 6*d* are aligned along the central longitudinal axis 1*a* and are coupled to the central shaft 5, associated with its external thread 5*f*.

As can be seen in the accompanying figures, the proximal wedge 6*p* and the distal wedge 6*d* each have two inclined surfaces 6'*p* and 6'*d*, each facing a respective plate 2 and 3. These inclined surfaces 6'*p* and 6'*d* lie on respective inclined planes, facing the internal surfaces 2*i* and 3*i* of the plates and converging towards a middle portion 1*m* of the cage.

The distal wedge 6*d* and the proximal wedge 6*p* have a central through housing 7, inside which the central shaft 5 is inserted.

Figure 11:
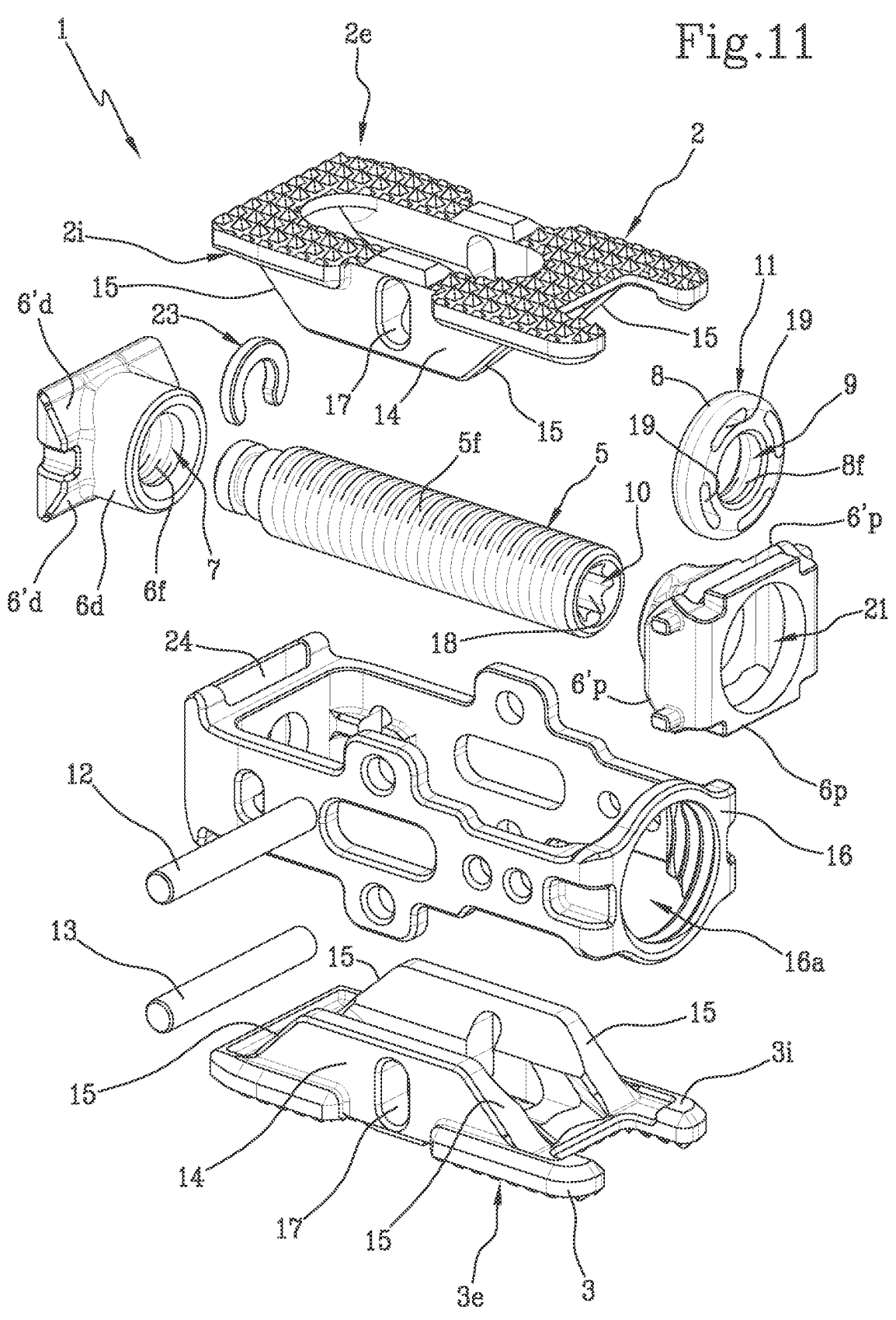
FIG. 11 shows an exploded view of the cage object of the present invention.

As can be best seen in the exploded view of FIG. 11, the distal wedge 6*d* comprises a threaded portion 6*f*, suitable to be screwed onto the external thread 5*f* of the central shaft 5. The threaded portion 6*f* of the distal wedge 6*d* is made on the surface delimiting the housing 7 inside which the central shaft 5 is inserted.

The proximal wedge 6*p*, on the other hand, has therein an annular disc 8 having a threaded portion 8*f* which couples with the external thread 5*f* of the central shaft 5. The annular disc 8 has a central circular cavity 9, placed at the housing 7 of the proximal wedge 6*p*. The threaded portion 8*f* of the annular disc 8 is made on the surface delimiting said circular cavity 9.

The annular disc 8 is contained within the proximal wedge 6*p*, caged therein, and can rotate about the central shaft 5 to promote the translation of the proximal wedge 6*p* along the central longitudinal axis 1*a*. The movement of the proximal wedge 6*p* and the distal wedge 6*d* will be explained in detail below.

The movement and adjustment mechanism 4 further comprises a first actuator 10 and a second actuator 11, both provided on the central shaft 5 and placed at the same proximal end 5*p* of said central shaft 5.

The first actuator 10 and the second actuator 11 can be actuated in a counter-rotating manner with respect to each other about the central longitudinal axis 1*a*. The first 10 and the second 11 actuator are active on the central shaft 5, on the distal wedge 6*d* and on the proximal wedge 6*p* to move, in translation along the central longitudinal axis 1*a*, the proximal wedge 6*p* and the distal wedge 6*d* so as to promote the translation and the inclination of the plates.

Specifically, and as will be described below, the first actuator 10 is suitable to rotate the central shaft 5 and to move the distal wedge 6*d* and the proximal wedge 6*p*.

The second actuator 11, on the other hand, is suitable to move only the proximal wedge 6*p*.

The proximal wedge 6*p* and the distal wedge 6*d* can be actuated, and are thus movable, both independently of each other and simultaneously, depending on the desired opening and relative position between the two plates. In other words, depending on how much it is wished to space out in parallel the plates or incline them, the two wedges are moved respectively simultaneously by a same pitch along the central shaft 5 or separately.

The cage 1 further comprises a first pin 12 and a second pin 13, each arranged transversely to the central longitudinal axis 1*a* and contained between the first 2 and the second 3 plate.

The first plate 2 and the second plate 3 rotate around respective hinge axes 2*a* and 3*a* passing through the pins 12 and 13.

The plates 2 and 3 vary their inclination symmetrically with respect to a plane of symmetry X passing through the central longitudinal axis 1*a*, interposed and parallel to the plates 2 and 3 when the cage is in the rest configuration or in the first operating configuration.

In the rest configuration or in the first operating configuration, the plane of symmetry X is equidistant from the two plates, while in the second and third operating configuration, the two plates are inclined and transverse to said plane of symmetry X, each defining with said plane X angles having the same amplitude, variable at will depending on the desired adjustment and required in the surgical phase. The two plates 2 and 3 are always axially symmetrical with respect to this plane of symmetry X.

In particular, the first 12 and the second 13 pin, around which the first plate 2 and the second plate 3 respectively rotate, are orthogonal to the central longitudinal axis 1*a* and parallel to the plane of symmetry X.

Each pin 12 and 13 therefore comprises a respective longitudinal axis 12*a* and 13*a*, orthogonal to the central longitudinal axis 1*a* and parallel to the plane of symmetry X, which each define a respective hinge axis 1*b* around which the first 2 and the second 3 plate respectively rotate.

The first plate 2 and the second plate 3 each have two projecting portions 14 protruding from the respective internal surfaces 2*i* and 3*i*, facing each other and turned internally to the cage 1. Each projecting portion 14, preferably in a number of two for each individual plate, is arranged along a respective major side of the first 2 and second 3 plate and extends parallel to the central longitudinal axis 1*a*. The two projecting portions 14 of each individual plate are parallel to each other.

These projecting portions 14 each have two inclined planes 15 along which the proximal wedge 6*p* and the distal wedge 6*d* slide to promote the movement of the first plate 2 and the second plate 3.

These inclined planes 15 are converging towards the middle portion 1*m* of the cage 1, to define, with the inclined planes of the opposite plate, respective V-shaped housings, having a vertex oriented towards the middle portion 1*m*. Each individual V-shaped housing houses a respective wedge (proximal or distal), which is movable slidingly therein.

In particular, the inclined surfaces 6'*p* and 6'*d* of the proximal wedge 6*p* and of the distal wedge 6*d* abut and slide against the inclined planes 15 of the two plates: the sliding of the proximal wedge 6*p* and/or of the distal wedge 6*d* along the central longitudinal axis 1*a* causes the inclined surfaces 6'*p* and 6'*d* of the two wedges, by abutting against the inclined planes 15 of the two plates and varying their relative position with respect to them, to interact with the latter pushing the plates towards the outside of the cage (thus causing their mutual spacing out), when the wedges advance, simultaneously or individually, towards the middle portion 1*m* of the cage, or acting as resting surfaces accompanying the plates to close (thus causing the cage to close), when the wedges move away, simultaneously or individually, from the middle portion 1*m*.

Figure 12:
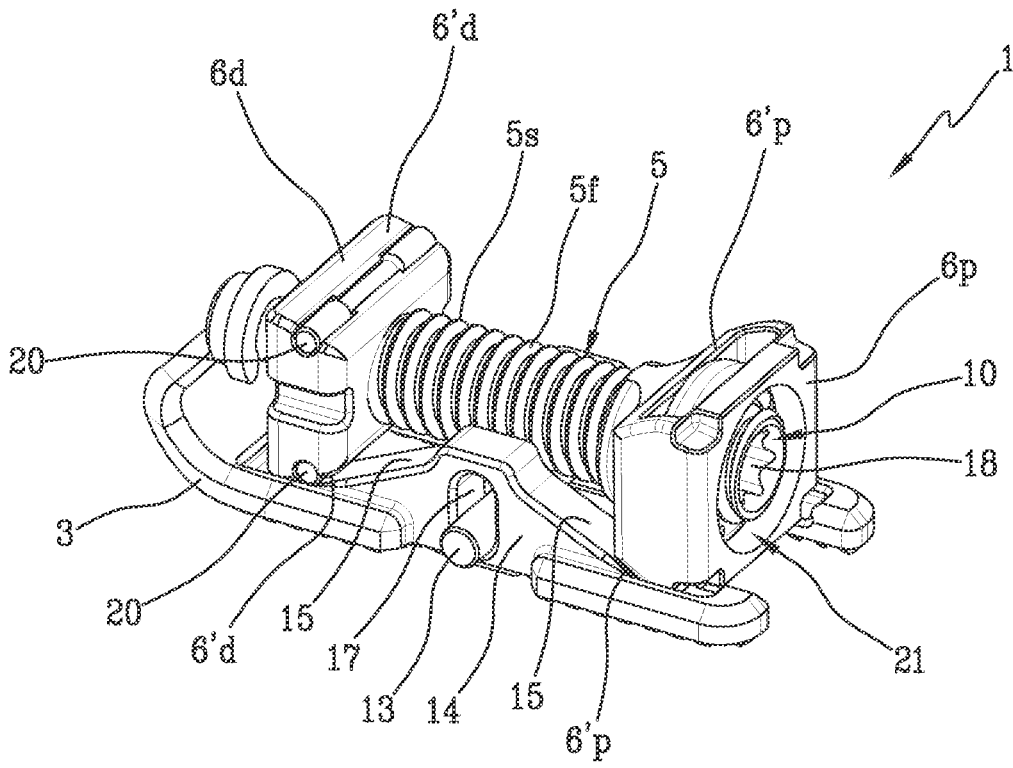
FIG. 12 shows an alternative configuration of the cage object of the present invention, with some parts removed to make the internal structure better visible.

In an alternative embodiment shown in FIG. 12, the distal wedge 6*d* may have two rollers 20 on the inclined surfaces 6'*d* which facilitate the surface sliding, reducing the friction thereof, between the inclined surfaces 6'*d* and the respective inclined planes 15.

The cage 1 further comprises a containment and connection structure 16, suitable to contain therein the movement and adjustment mechanism 4, the central longitudinal shaft 1*a*, the distal wedge 6*d* and the proximal wedge 6*p*. This containment structure 16 is interposed between the first 2 and the second 3 plate in a perimeter position, such as to surround the cage on the four sides laterally, and is suitable to connect the first 2 and the second 3 plate to each other. The latter remain outside this containment structure 16, above and below it.

The containment structure 16 has, at the proximal end 1*p* of the cage, an opening 16*a*, such as a window made in the containment structure 16 itself, to be able to access the proximal portion 5*p* of the central shaft 5 and to the proximal wedge 6*p*.

The central shaft 5 is connected to the containment structure 16 by means of a ring 23 which blocks by interference the distal end 5*d* of the central shaft 5, around which the ring 23 is placed, inside a seat 24 made in the containment structure 16.

The first pin 12 and the second pin 13, arranged transversely to the central longitudinal axis 1*a*, are contained between the first 2 and the second 3 plate and extend between two projecting portions 14 of each individual plate.

Furthermore, each pin 12 and 13 connects the respective plate 2 and 3 to the containment and connection structure 16.

Each projecting portion 14 of both the first 2 and second 3 plate centrally has a respective eylet 17 extending orthogonally to the central longitudinal axis 1*a*, elongated towards the opposite plate.

The pins 12 and 13 are inserted in these eyelets 17, to allow the movement of the first 2 and the second 3 plate by moving mutually away from, and closer to each other.

The two pins 12 and 13 remain in a fixed position, while the two plates 2 and 3 translate with respect to these pins thanks to the play offered by the elongated oval slots.

The movement of the proximal wedge 6*p* and the distal wedge 6*d* is caused by the first actuator 10 and the second actuator 11, both provided on the central shaft 5 and placed at the same proximal end 5*p* of said central shaft 5.

The first actuator 10 is placed at the proximal end 5*p* of the central shaft 5. Specifically, as can be seen, for example, in FIGS. 1, 5 and 7, the first actuator 10 is defined by a polygonal housing 18 made axially in the central shaft 5; this polygonal housing 18 is suitable to receive by interference coupling a gripping and actuating tool.

The second actuator 11, on the other hand, is placed inside the proximal wedge 6*p*. Specifically, the second actuator 11 is the annular disc 8 described above. Said annular disc 8 is fitted onto the central shaft 5 and, as mentioned before, has an internal thread 8*f* which couples with the external thread 5*f* of the central shaft 5.

The annular disc 8 has gripping portions 19 suitable to receive by coupling a gripping and actuating tool.

In use, the position of the plates is adjusted as follows.

FIGS. 1 and 2 show the cage object of the present invention in a non-operating configuration, with the distal wedge 6*d* and the proximal wedge 6*p* placed respectively at the distal end 5*d* and at the proximal end 5*p* of the central shaft 5, therefore in the position of maximum mutual spacing out, and the plates completely closed, parallel and in the position of maximum mutual approach.

By inserting the gripping and actuating tool inside the polygonal housing 18, through the opening 16*a* of the containment structure 16, the rotation of the central shaft 5 can be promoted. The gripping and actuating tool meshes in the polygonal housing 18 and, by turning it in one direction, e.g. clockwise, it rotates the central shaft 5 around the central longitudinal axis 1*a*. The single rotation of the central shaft 5, which has a single thread 5*f* with a single winding direction, causes the translation of the distal wedge 6*d* and of the proximal wedge 6*p* towards the same end, or towards the proximal end or towards the distal end, of the shaft itself. In other words, by rotating only the central shaft 5, the simultaneous translation, along the same direction, of the two wedges is actuated by the same quantity along the central longitudinal axis 1*a*.

Therefore, in order to be able to move the two wedges in the opposite direction, therefore in approach to the middle portion 1*m* in case it is wished to open the cage by translating the first and the second plate parallel to each other and in mutual distancing, one must also act on the annular disc by applying a double counter-rotating rotation with respect to the direction of rotation imposed on the central shaft.

The distal wedge 6*d* meshes directly on the thread 5*f* of the central shaft 5 and therefore it is actuated directly and only by the rotation imposed on the central shaft 5: a turn of the shaft advances the distal wedge 6*d* by a pitch N.

The proximal wedge 6*p*, on the other hand, does not mesh directly on the central shaft 5, therefore, in order to advance it in the opposite direction to that along which the distal wedge translates, it is necessary to act on the annular disc 8. With the same gripping and actuating tool, inserted in the polygonal housing 19 of the central shaft 5 in order to rotate the latter, one acts simultaneously also the annular disc 8, rotating it in the opposite direction to the direction of rotation imposed on the central shaft 5. The counter-rotating rotation, between the annular disc 8 and the central shaft 5, is necessary to translate the two wedges along the same axial direction, caused by the central longitudinal axis 1*a*, but in opposite directions. Specifically, in order to advance the proximal wedge 6*p* towards the middle portion 1*m* by the same pitch N by which the distal wedge 6*d* was shifted, two rotations must be applied to the annular disc 8 in the opposite direction to the direction of rotation applied to the central shaft 5. In fact, a rotation given to the annular disc 8 in a counter-rotating direction with respect to the direction of rotation of the central shaft 5 cancels the rotation of the central shaft 5 which would cause the translation of the proximal wedge 6*p* in the same direction along which the distal wedge moves, while the second rotation imposed on the annular disc 8 causes the effective translation of the annular disc 8, and therefore of the proximal wedge 6*p*, by a pitch N in the opposite direction to that along which the distal wedge moves. Therefore, if one wishes to increase the height of the cage, by moving the plates away, one will act, through the first actuator 10, on the central shaft 5 by applying a certain number of turns K which will cause the translation of the distal wedge 6*d* by a certain number of pitches Nx towards the middle portion 1*m*, and at the same time twice the turns and in the opposite direction ($-2K$) will be applied to the annular disc 8, so as to cause the proximal wedge to translate by the same number of pitches Nx towards the middle portion 1*m*.

The annular disc 8 is contained, as described above, within the body of the proximal wedge 6*p* and is free to rotate therein. The proximal wedge 6*p* has an opening 21, turned outwards from the cage, through which it is possible to access the gripping portions 19 of the annular disc 8.

The rotation of the annular disc 8 around the central shaft 5 causes its translation along the central longitudinal axis 1*a*: by shifting along the central longitudinal axis, the annular disc 8, caged inside the proximal wedge 6*p*, drags the proximal wedge 6*p* with it in axial translation.

By bringing the wedges closer to the middle portion 1*m* of the cage by the same number of pitches, the first 2 and the second 3 plate shift parallel to each other moving away from each other to the central shaft 5, as shown in FIGS. 3 and 4. This takes place because, following the axial translation towards the middle portion 1*m*, then by sliding the wedges towards the vertex of the respective V-shaped housing, the inclined surfaces 6'*p* and 6'*d* of the distal wedge 6*d* and proximal wedge 6*p* slide against the inclined planes 15 causing the two plates to be spaced out.

If it is wished to close the plates, by shifting the wedges away from each other by the same number of pitches N, one acts exactly in the opposite way imposing a rotation opposite to that previously given to the central shaft 5 and a double rotation, always counter-rotating with respect to the rotation given at that time to the central shaft 5, to the annular disc 8. In this way the wedges move away from each other, returning to the initial position at the distal end 5*d* and proximal end 5*p*, bringing the plates 2 and 3 closer to each other.

If the cage is to be opened so as to have a diverging inclination of the plates towards the proximal end 1*p* of the cage 1, as can be seen in FIGS. 5 and 6, the proximal wedge 6*p* will be advanced towards the middle portion 1*m*.

To do this, assuming starting from the non-operating configuration shown in FIG. 1 and wishing to open the cage in a diverging way towards the proximal end 1*p*, the central shaft 5 must be kept stationary and the annular disc 8 must be rotated so as to advance the proximal wedge 6*p* towards the middle portion 1*m*.

Conversely, if the cage is to be opened so as to have a diverging inclination of the plates towards the distal end 1*d* of the cage 1, as can be seen in FIGS. 7 and 8, the distal wedge 6*dp* will have to be advanced towards the middle portion 1*m*.

To do this, assuming starting from the non-operating configuration shown in FIG. 1 and wishing to open the cage in a diverging way towards the distal end 1*d*, the central shaft 5 must be rotated in a direction such as to cause the advancement of the distal wedge 6*d* towards the middle portion and the annular disc 8 must be rotated in the opposite direction by the same number of turns imparted to the central shaft 5. This is because in order to make the cage open towards the distal end 1*d*, I have to keep the proximal wedge 6*p* stationary: this happens if I cancel the rotation of the central shaft 5 by counter-rotating, by the same number of turns, the annular disc 8.

Depending on the starting position of the wedges 6*d* and 6*p*, therefore depending on where the wedges are placed along the central shaft 5, one or the other wedge must be shifted towards the middle portion 1*m* of the cage and/or towards the distal 1*d* and/or proximal 1*p* end, considering that the distal wedge 6*d* is actuated only by the rotation of the central shaft 5 and that a rotation in one direction of the central shaft 5 causes the translation of the distal wedge 6*d* by a pitch N towards the middle portion 1*m* or towards the distal end 1*d*, while the shift of the proximal wedge 6*p* is caused both by the rotation of the central shaft 5, and by the rotation of the annular disc 8 around the central shaft 5; therefore, depending on whether or not the central shaft 5 is being rotated, and bearing in mind the direction along which the proximal wedge is to be translated and by how many pitches it is to be shifted, it must be assessed whether the rotation of the shaft 5 must be cancelled or not. If the two wedges are to be shifted in the same direction, then both towards the distal end 1*d* or towards the proximal one 1*p*, so as to keep the distance between them constant, one will only act on the central shaft 5 since, in this case, it will not be necessary to cancel the rotation of the central shaft 5 with the double counter-rotation of the annular disc 8.

In the event that the proximal wedge 6*p* reaches the end of the stroke against the containment structure 16, but it is necessary to further translate the distal wedge 6*d* towards the middle portion 1*m*, it will be necessary to rotate the annular disc 8 in the opposite direction to the rotation given by the central shaft 5 and according to a greater number of turns so as to cause the translation of the proximal wedge 6*p* towards the middle portion 1*m* and, subsequently, to rotate again only the central shaft 5 to move the two wedges towards the proximal end 1*p* again in unison.

The invention achieves the intended purposes in that the cage described has a structure such as to allow a rapid, simple and precise adjustment of the opening and/or inclination of the plates, which allows a correction of the intervertebral distance and/or the curvature of the spine, to restore the correct anatomy of the patient. The particular position of the actuators, placed at a same end, allows the surgeon to immediately access the adjustment site.

The double actuators guarantee an easy and immediate adjustment of the position of the wedges and, therefore, a precise and punctual variation of the distance between the plates and their mutual inclination.

The central shaft having a single thread with a single winding direction allows a faster assembly of the component, as well as giving the possibility to maximize the dimensions of the threaded shaft compared to the rest of the cage. In fact, on the contrary, if one had two threads, one would have a mechanical stop between the two to prevent a wedge, having reached the end of the stroke, from disengaging from the respective thread. Thus, compared to what is shown in the prior art, with a single mono-directional thread there is less mechanical processing (which creates stress in the shaft), more resistance, less removal of material, greater production speed and lower production costs.

The cage described is also compact, solid and allows the use of an appropriate adjustment tool capable of overcoming the resistance offered by the vertebrae that weigh on the plates of the cage, without the surgeon having to apply an excessive force and without the risk of breakage of the cage and of the adjustment tool. This is achieved thanks to the position of the actuators that are brought close to the surgeon, in a position that allows to have a greater amplitude of the coupling portions themselves between the cage and the gripping and adjustment tool.

The invention claimed is:

1. An expandable intervertebral fusion cage for spacing out two vertebral bodies of a vertebral column, comprising:
a first plate and a second plate opposite to the first plate, both having a planar conformation axially elongated along a central longitudinal axis extending from a proximal end to a distal end of said cage, wherein said first plate and said second plate comprise respective internal surfaces facing each other and respective external contact surfaces, the latter being suitable to receive a respective vertebral body for resting;
a movement and adjustment mechanism of said first plate and said second plate, suitable to promote the mutual translation of said first plate and said second plate parallel to each other, so as to vary the height of the cage to space out two adjacent vertebral bodies, and the rotation of the one with respect to the other around a respective hinge axis, placed transversally to the central longitudinal axis of the cage and contained between said first plate and said second plate, so as to vary the mutual inclination of said first plate and said second plate to correct the deformation of the vertebral column;
wherein said movement and adjustment mechanism comprises a single central shaft, coaxial with said central longitudinal axis and having an external thread, a proximal wedge and a distal wedge placed between said first plate and said second plate, aligned along said central longitudinal axis and coupled to the external thread of said central shaft which is centrally inserted in said distal wedge and said proximal wedge;
wherein said movement and adjustment mechanism further comprises a first actuator and a second actuator, both provided on said central shaft and placed at the same proximal end of said cage, wherein said central shaft, suitable to rotate about said central longitudinal axis, has a single external thread having a single mono-directional winding direction, extending throughout the external surface of said central shaft;
wherein said second actuator is an annular disc entirely contained inside the proximal wedge and fitted onto said central shaft, said annular disc having an internal thread that couples with the external thread of said central shaft;
wherein said annular disc is free to rotate about said central shaft to promote the translation of said proximal wedge along said central longitudinal axis by meshing with the external thread of said central shaft that is within said proximal wedge and dragging said proximal wedge in translation towards said proximal end or towards the middle portion of said cage.

2. The expandable intervertebral fusion cage according to claim 1, wherein said distal wedge comprises a threaded portion suitable to be screwed onto said external thread of said central shaft.

3. The expandable intervertebral fusion cage according to claim 1, wherein said first actuator and said second actuator can be actuated in a counter-rotating manner with respect to each other about said central longitudinal axis.

4. The expandable intervertebral fusion cage according to claim 1, wherein said proximal wedge and said distal wedge are movable both independently of each other and simultaneously, depending on the desired opening and relative position between said first plate and said second plate.

5. The expandable intervertebral fusion cage according to claim 1, wherein said first plate and said second plate each have two projecting portions, protruding from said respective internal surfaces which face each other and are turned internally to the cage, having inclined planes along which said proximal wedge and said distal wedge slide to promote the movement of said first plate and said second plate in mutual translation and/or rotation.

6. The expandable intervertebral fusion cage according to claim 5, wherein said inclined planes are converging towards a same middle portion of the cage, to define, with the inclined planes of the opposite plate, respective V-shaped housings, having a vertex oriented towards said middle portion of the cage and within which said proximal wedge and said distal wedge slide.

7. The expandable intervertebral fusion cage according to claim 5, wherein the expandable intervertebral fusion cage comprises a containment and connection structure suitable to contain therein said movement and adjustment mechanism, said central shaft, said distal wedge and said proximal wedge and to connect said first plate and said second plate with each other; said containment and connection structure being interposed between said first plate and said second plate in a perimeter position.

8. The expandable intervertebral fusion cage according to claim 7, wherein the expandable intervertebral fusion cage comprises two pins, each one arranged transversally to said central longitudinal axis and contained between said first plate and said second plate.

9. The expandable intervertebral fusion cage according to claim 8, wherein each pin connects the respective plate to said containment and connection structure.

10. The expandable intervertebral fusion cage according to claim 9, wherein said projecting portions of said first plate and of said second plate each centrally have a respective eyelet, extending orthogonally to said central longitudinal axis and extending towards the opposite plate.

11. The expandable intervertebral fusion cage according to claim 10, wherein said pins are inserted in said eyelets to allow moving said first plate and said second plate; said first plate and said second plate translating parallel to each other moving mutually away from, and closer to each other, and rotating with respect to each other about the respective pin, to incline so as to diverge or converge towards the distal end.

12. The expandable intervertebral fusion cage according to claim 1, wherein said first actuator is suitable to rotate said central shaft and move said distal wedge and said proximal wedge.

13. The expandable intervertebral fusion cage according claim 1, wherein said second actuator is suitable to move said proximal wedge.

14. The expandable intervertebral fusion cage according to claim 1, wherein said first actuator is placed at a proximal end of said central shaft.

15. The expandable intervertebral fusion cage according to claim 14, wherein said first actuator is defined by a polygonal housing axially made in the central shaft, for inserting a gripping and actuating tool.

16. The expandable intervertebral fusion cage according to claim 1, wherein said annular disc has gripping portions for engaging with a gripping and actuating tool.

*   *   *   *   *